United States Patent [19]

Borschel et al.

[11] Patent Number: 5,021,245

[45] Date of Patent: Jun. 4, 1991

[54] INFANT FORMULA CONTAINING A SOY POLYSACCHARIDE FIBER SOURCE

[75] Inventors: Marlene W. Borschel, Worthington; John D. Benson, Dublin; Merle D. Breen, Westerville; William C. MacLean, Jr., Upper Arlington; Debra L. Ponder, Worthington, all of Ohio; Alan D. Strickland, Dallas, Tex.; William R. Treem, Avon, Conn.

[73] Assignee: Abbott Laboratories, Abbott Park, Ill.

[21] Appl. No.: 526,912

[22] Filed: May 22, 1990

[51] Int. Cl.$^5$ ................................................ A23C 9/20
[52] U.S. Cl. ........................................ 426/2; 426/598; 426/801
[58] Field of Search .................... 426/801, 598, 585, 2

[56] References Cited

U.S. PATENT DOCUMENTS 4,614,663  9/1986  Rule .................................... 426/801

FOREIGN PATENT DOCUMENTS 2142340  1/1985  United Kingdom ................ 426/801

Primary Examiner—Carolyn Paden
Attorney, Agent, or Firm—D. O. Nickey; L. R. Drayer; E. H. Gorman, Jr.

[57] ABSTRACT

A novel liquid nutritional for use as an infant formula for use in the treatment of infantile colic is disclosed. The formula comprises protein, fat, carbohydrates and dietary fiber of a concentration of between 3.1 and 14.1 grams of fiber per liter of formula. Specific preferred protein, fat, carbohydrate and fiber sources are disclosed. Also disclosed is a method of treating infants with colic by feeding an infant the formula made in accordance with the invention. Also disclosed is a method for manufacturing the infant formula of the invention.

17 Claims, No Drawings

INFANT FORMULA CONTAINING A SOY POLYSACCHARIDE FIBER SOURCE

TECHNICAL FIELD

The present invention relates generally to a liquid nutritional product, and more particularly, to an infant formula for use in the management of infantile colic.

BACKGROUND ART

Colic is one of the most confusing subjects facing pediatrics today. In the absence of a standard definition of "colic" it is difficult to compare one study on "colicky infants" with another. Furthermore, given the absence of a standard definition, studies assessing the causes and/or management of colic undoubtedly involve a heterogeneous group of infants with both a variety of problems as well as no problem at all.

Numerous reports in the pediatric literature suggests that colic occurs in at least 10% to as high as 30% of both breast-fed and formula-fed infants. Colic is often described as unexpected paroxysms of crying or fussing which generally occur in the evening hours. These episodes begin in the first weeks of life and often subside by the time the infant reaches 3-4 months of age. In normal infants, crying and fussing behavior peaks at 2.75 hours per day at 6 weeks of age. Colicky infants are often defined as those infants who cry and fuss for more than 3 hours per day at 6 weeks of age, although it must be recognized that this is not a uniform definition. Even when colic has been defined, many studies have not documented it in their own study subjects prior to attempts at treatment.

A significant amount of literature on colic is directed toward the discovery of an organic or physical cause of the presumed pain. Examples of suggested causes include the assumption that the infant is suffering gastrointestinal pain from the maldigestion of carbohydrate, abnormal gastrointestinal motility, immaturity of the gastrointestinal tract or the central nervous system, allergy to cow-milk protein, or gastroesophageal reflux. Alternatively, an equal body of literature proposes a non- organic etiology for colic, such as the intrinsic temperament of the infant coupled with maternal-/caretaker maladaption or psychological problems.

Currently several relatively diverse therapies are employed in attempts to treat colic. To some, the most effective treatment of colic is parental counseling whereby the parental reaction to a child's crying is modified in the belief that this parental reaction actually aggravates the situation. To those who believe that colic is somehow related to a food allergy to intact protein, certain formulas incorporate hydrolysates, wherein the protein in the formula is broken down to reduce the allergenic response. However, this specific method of treatment is both very expensive and questionable as to its effectiveness. To those who believe that colic is related to an immature nervous system being overloaded, another current therapy often employs sedative or anti-spasmodic drugs. Still another therapy used in the treatment of colicky infants involves the use of mechanical rocking or vibrating devices. Unfortunately, each of these treatments is often ineffective and hence can increase parental anxiety. Increased anxiety has led to reports in the literature of parental abuse of the colicky infant. Regardless of the treatment, an infant who suffers from colic typically cries and fusses for more than 3 hours each day over an approximate 3 to 4-month period of time.

Fiber is a normal dietary constituent once solid foods become part of the diet and the child is no longer exclusively milk-fed, generally after 4 to 6 months of age. Typically fiber is introduced into the infant's diet only after the infant is consuming solid foods such as cereals, fruits and vegetables which contain fiber. As such, dietary fiber would not normally be a constituent of the diet of infants who experience colic.

Prior to the present invention, fiber has not been intentionally incorporated into infant formula for the specific treatment of colicky infants. In fact, no dietary treatment has been conclusively documented in controlled double-blinded studies as alleviating infantile colic. Increased fiber has been added to the diets of older infants, i.e. those older than 6 months of age, and toddlers for the treatment of diarrhea and constipation. In addition, dietary fiber has been successfully used in adults to treat numerous conditions.

It is thus apparent that the need exists for an improved infant formula that will significantly decrease the symptoms of colic in a significant number of infants.

DISCLOSURE OF THE INVENTION

There is disclosed an infant formula, said formula comprising: 1) protein, said protein being of a concentration of between 10 and 25 grams per liter of formula; 2) fat, said fat being of a concentration of between 20 and 45 grams per liter of formula; 3) carbohydrates, said carbohydrates including those from total dietary fiber being of a concentration of between 60 and 110 grams per liter of formula; and 4) total dietary fiber, said fiber being of a concentration of between 3.1 and 14.1 grams per liter of formula.

As used herein, total dietary fiber content is determined by the AOAC method as set forth in Prosky, L, Asp, N-G, Schweizer, TF, DeVries, JW and Furda, I, "Determination of Insoluble, Soluble, and Total Dietary Fiber in Foods and Food Products: Interlaboratory Study", *J. Assoc. Off. Anal. Chem.*, 1988.

The fiber source utilized in this invention is soy polysaccharide derived from soy beans, also known as soya beans.

Preferably the protein has as its source soy protein isolate, or sodium and calcium caseinates or a blend thereof; said fat has as its source soy, coconut or corn oil or another vegetable oil or a blend thereof; and said carbohydrates other than total dietary fiber have as their source sucrose, corn syrup, glucose polymers, other carbohydrates or a blend thereof.

Preferably, the protein is of a concentration of between 15 and 21 grams per liter of formula, said fat is of a concentration of between 23 and 40 grams per liter of formula, and said carbohydrates including total dietary fiber are of a concentration of between 70 and 110 grams per liter of formula. More preferably, said protein is of a concentration of between 15 and 20 grams per liter of formula, said fat is of a concentration of between 24 and 38 grams per liter of formula, said carbohydrates including total dietary fiber are of a concentration of between 75 and 110 grams per liter of formula, and said total dietary fiber is of a concentration of between 3.5 and 14.0 grams per liter of formula.

In a preferred embodiment of the invention, said protein is of a concentration of approximately 19.6 grams per liter of formula and has as its source soy protein isolate, said fat is of a concentration of approximately 37.4 grams per liter of formula and has as its source a blend of soy and coconut oils, and said carbohydrates including total dietary fiber are of a concentration of approximately 75.9 grams per liter of formula and except for those from dietary fiber have as their source sucrose or corn syrup or a blend thereof. In this formula, the fat provides 50% of the calories and the carbohydrates (minus those from dietary fiber) provide 40% of the calories in the formula.

In one embodiment of the invention, the protein is of a concentration of approximately 20.3 grams per liter of formula and has as its source a blend of sodium and calcium caseinates and soy protein isolate, said fat is of a concentration of approximately 24.7 grams per liter of formula and has as its source corn oil, and said carbohydrates including total dietary fiber are of a concentration of approximately 106.6 grams per liter of formula and excluding total dietary fiber have as their source a blend of sucrose and glucose polymers. In this formula, said fat provides 32% of the calories and said carbohydrates (minus those from dietary fiber) provide 57% of the calories.

There is also disclosed a method of treating infants with colic, said method consists of feeding an infant in need of treatment a formula, the improvement comprising a formula consisting essentially of: 1) protein, said protein being of a concentration of between 10 and 25 grams per liter of formula; 2) fat, said fat being of a concentration of between 20 and 45 grams per liter of formula; 3) carbohydrates, said carbohydrates including total dietary fiber being of a concentration of between 60 and 110 grams per liter of formula; and 4) total dietary fiber, said fiber being of a concentration of between 3.1 and 14.1 grams per liter of formula. In this formula the fiber source is limited to soy polysaccharide.

The formula utilized in this method has as its protein source soy protein isolate, or sodium and calcium caseinates or a blend thereof; said fat has as its source soy, coconut, corn, or another vegetable oil or a blend thereof; and said carbohydrates besides those from total dietary fiber, preferably have as their source sucrose, corn syrup, glucose polymers, or other carbohydrates or a blend thereof.

In the formula used in this method, preferably said protein is of a concentration of between 15 and 21 grams per liter of formula, said fat is of a concentration of between 23 and 40 grams per liter of formula, and said carbohydrates including total dietary fiber are of a concentration of between 70 and 110 grams per liter of formula. More preferably said protein is of a concentration of between 15 and 20 grams per liter of formula, said fat is of a concentration of between 24 and 38 grams per liter of formula, said carbohydrates including total dietary fiber are of a concentration of between 75 and 110 grams per liter of formula, and said fiber is of a concentration of between 3.5 and 14.0 grams per liter of formula.

In one embodiment of the invention utilizing this method, the formula consists of protein which is of a concentration of approximately 19.6 grams per liter of formula and has as its source soy protein isolate, said fat is of a concentration of approximately 37.4 grams per liter of formula and has as its source a blend of soy and coconut oils, and said carbohydrates including total dietary fiber are of a concentration of approximately 75.9 grams per liter of formula and have as their source, other than that from dietary fiber, sucrose or corn syrup or a blend thereof. In this formula, the fat provides 50% of the calories and said carbohydrates (minus those from total dietary fiber) provide 40% of the calories.

In a modified embodiment of the formula utilized in the inventive method of treating infants with colic, said protein is of a concentration of approximately 20.3 grams per liter of formula and has as its source a blend of sodium and/or calcium caseinates and soy protein isolate, said fat is of a concentration of approximately 24.7 grams per liter of formula and has as its source corn oil, and said carbohydrates including total dietary fiber are of a concentration of approximately 106.6 grams per liter of formula and have as their source besides that from total dietary fiber a blend of sucrose and glucose polymers. In the modified embodiment of the formula, the fat provides 32% of the calories and the carbohydrates (minus those from total dietary fiber) provide 57% of the calories.

There is also disclosed a method for manufacturing infant formula, said method comprising the steps of: 1) dispersing in an appropriate quantity of a protein source in water sufficient to solubilize the protein, thereby forming a protein solution; 2) dissolving carbohydrates in water, thereby forming a carbohydrate solution; 3) mixing minerals in water, thereby forming a mineral solution; 4) dispersing fiber in a sufficient quantity of water to form a low viscosity solution, thereby forming a fiber solution, 5) combining appropriate quantities of said protein solution, said carbohydrate solution, said mineral solution, said fiber solution, and a solution of vegetable oil containing oil soluble vitamins, 6) heat processing and homogenizing the combined solution; 7) adding water soluble vitamins to the combined solution; and 8) adding water to dilute the combined solution to the desired caloric density, approximately 670–725 kcal per liter of formula with the total dietary fiber content of said formula being between 3.1 and 14.1 grams per liter of formula. Furthermore, the fiber source used in this method is soy polysaccharide.

One aspect of the present invention provides a complete infant formula that will significantly decrease the symptoms of colic in a significant number of infants.

Another aspect of the invention is that this formula is nutritionally complete as an infant feeding.

Yet another aspect of the invention resides in the relatively easy and cost-effective method for manufacturing a pediatric nutritional.

Other aspects and advantages of the instant invention will be apparent from the following description, examples, and the appended claims.

DETAILED DESCRIPTION OF THE INVENTION

Specifically, the present invention is concerned with a liquid nutritional for infants which has been formulated so as to alleviate the symptoms of colic. The present invention is also concerned with the discovery of a method for management of colicky infants by the feeding of an infant formula having a very particular composition. The present invention is also concerned with a method for making the infant formula as herein disclosed.

The infant formula has as one of its main differences from the prior art, a very specific range of total dietary fiber and a specific source of fiber. It has been discovered that fiber content above or below this range provides unacceptable or ineffective results in the treatment of infantile colic.

Although fiber has been prescribed for older infants and toddlers for the treatment of diarrhea and constipation, it has been discovered that superior results can be achieved in the treatment of infantile colic by the inclusion of between 3.1 and 14.1 grams of total dietary fiber per liter of infant formula. This is somewhat surprising given the commonly accepted wisdom that fiber should not be added to an infant's diet until the infant is taking solid food such as cereal.

The advantages of using an infant formula to alleviate the symptoms of colic in infants are numerous. First, the formula would be readily available to parents and could be used as a first or second alternative if the infant displays colicky symptoms to other formulas. This would eliminate the numerous formula changes that are characteristic of the treatment of some colicky infants, wherein the infant may be fed 3 to 5 different formulas in the hope that the symptoms of colic can be alleviated under a food allergy or gastrointestinal dysfunction theory. One undesirable side affect of this frequent and relatively indiscriminant experimentation wi&h formula changes in response to concerns about the crying of a colicky infant is that it often causes parents to believe that their children are medically vulnerable and that they suffer from a disease or illness. A second advantage of using infant formula to alleviate the symptoms of colic in infants is that the use of drugs, which have not been proven to be particularly efficacious in the treatment of colic, could be reduced or eliminated.

One aspect of the present invention resides in the discovery that total dietary fiber administered to infants within specific ranges as part of the formula is effective in the treatment of infantile colic for the majority of infants. Levels of less than 3.1 grams of total dietary fiber per liter of formula have been demonstrated to be ineffective in the treatment of colic. While levels above 14.1 grams of total dietary fiber per liter of formula have been found effective, they have been deemed unacceptable due to abnormal stools resulting from this level of fiber intake.

The additive fiber source for the formulas of this invention was soy polysaccharide. The scope of this invention is limited to soy fiber since the state of the art does not allow one skilled in the art to predict with any level of certainty the effect of other fiber sources or the efficacious levels for these other sources of fiber. The particular soy polysaccharide used in this invention is preferably FIBRIM 300 ®, a product of Protein Technologies International. The nutrient composition of this particular soy polysaccharide as provided by the manufacturer is shown in the following Table I.

TABLE I

| Approximate Composition of FIBRIM 300 ® | |
|---|---|
| Nutrient | FIBRIM 300 ® per 100 g |
| Protein | 11.6 g |
| Fat | 1.0 g |
| Carbohydrate | 71.0 g |
| Ash | 6.5 g |
| Moisture | 6.5 g |
| Calcium | 440 mg |
| Phosphorus | 330 mg |
| Magnesium | 220 mg |
| Sodium | 250 mg |
| Potassium | 870 mg |
| Chloride | 170 mg |
| Iron | 12.0 mg |
| Zinc | 2.2 mg |
| Copper | 0.26 mg |

TABLE I-continued

| Approximate Composition of FIBRIM 300 ® | |
|---|---|
| Nutrient | FIBRIM 300 ® per 100 g |
| Thiamin | 0.09 mg |
| Riboflavin | 0.22 mg |
| Pyridoxine | 0.008 mg |
| Niacin | 0.093 mg |
| Folic Acid | 5.47 mcg |
| Pantothenic Acid | 0.017 mg |
| Biotin | 0.054 mg |
| Choline | 85 mg |
| Inositol | 121 mg |
| Dietary Fiber | 78.2 g |

Furthermore, the fiber composition of the preferred soy polysaccharide used in this invention has been analyzed by several investigators with the results of some of these analyses presented in the following Table II. The varying percentages of the constituents is largely due to variation of the analytical methods and may also reflect possible changes in the composition of the product over time.

TABLE II

| Composition of Soy Polysaccharide FIBRIM 300 ® by Various Investigators | | | | | |
|---|---|---|---|---|---|
| | Study | | | | |
| Constituent | #1 | #2 | #3 | #4 | #5 |
| | Percent Dry Weight | | | | |
| Total Dietary Fiber | 70.7 | 78.2 | 76.9 | 65.6 | 75.0 |
| Neutral Detergent Fiber | 30.4 | NA | NA | 49.5 | 40.0 |
| Acid Detergent Fiber | 13.7 | NA | NA | NA | NA |
| Lignin | 5.2 | 2.6 | NA | 0.5 | 0.5 |
| Soluble Dietary Fiber | NA | 4.8 | 3.8 | 1.3 | NA |
| Cellulose | 8.5 | NA | NA | 14.3 | 10.0 |

Sources of Data:
1 - Independent analyses conducted in the lab of George Fahey, PhD, Department of Animal Sciences, University of Illinois. Analysis by methods of Goering, HK and Van Soest, PJ, "Forage Fiber Analyses Apparatus, Reagents, Procedures, and Some Applications)", USDA-ARS Handbook No. 379, ARS, USDA Washington, 1970, Prosky, L, Asp, N-G, Furda, I, et al, "Determination of Total Dietary Fiber in Foods and Food Products: Collaborative Study", J. Assoc. Off. Anal. Chem., 1985, and Li, BW and Andrews, KW, "Simplified Method for Determination of Total Dietary Fiber in Foods", J. Assoc. Off. Anal. Chem., 1988.
2 - Shinnick, FL, Hess, RL, Fischer, MH and Marlett, JA, "Apparent Nutrient Absorption and Upper Gastrointestinal Transit with Fiber-Containing Enteral Feedings", Am. J. Clin. Nutr., 1989. Analysis by modification of Theander method, see Shinnick, Fl, Longacre, MJ, Ink, SL, and Marlett, JA, "Oat Fiber: Composition vs. Physiological Function", J. Nutr., 1988.
3 - Steinke, FH, "Composition and Nutritional Value of Fibrim ® Soy Fiber (Soy Polysaccharide)", The Role of Dietary Fiber in Enteral Nutrition, Abbott Int'l. Ltd., Abbott Park, Ill., 1988. Analysis by method of Prosky, L., Asp, N-G, Furda, I, et al, "Determination of Total Dietary Fiber in Foods and Food Products: Collaborative Study," J. Assoc. Off. Anal. Chem., 1985.
4 - Steinke, FH, "Composition and Nutritional Value of Fibrim ® Soy Fiber (Soy Polysaccharide)", The Role of Dietary Fiber in Enteral Nutrition, Abbott Int'l. Ltd., Abbott Park, Ill., 1988. Analysis by method of Southgate, DAT, "The Measurement of Unavailable Carbohydrates: Structural Polysaccharides", Determination of Food Carbohydrates, Applied Science Publications Ltd, London, 1976.
5 - Taper, Milam, RS, McCallister, MJ et al, "Mineral Retention in Young Men Consuming Soy-Fiber-Augmented Liquid- Formula Diets", Am. J. Clin. Nutr, 1988. Neutral detergent fiber analysis by the method of Van Soest, PJ and McQueen, RW, "The Chemistry and Estimation of Fiber", Proc. Nutr. Soc., 1973. Total dietary fiber analyzed by the method of Southgate, DAT, "Determination of Carbohydrates in Foods", J. Sci. Food Agric., 1969.

Soy polysaccharide has been used in adult nutritionals and has been found to be safe. It has been assumed for purposes of illustrating this invention that the tested infant is normal and healthy except for the presence of infantile colic.

The effectiveness of alternative fibers in the treatment of colic is unknown. There are many types of fiber each having different physiological functions. For example, large chunks of wheat bran fiber do not cause the human body to behave in the same manner as large quantities of small particles of wheat bran fiber. Even fibers with similar monomeric sugar compositions can vary significantly in physiological function due to differing chemical linkages and processing treatments. It is for this reason that the teachings of this invention should not be applied to fiber sources other soy fiber.

The infant formula of this invention comprises protein, fat, carbohydrates, and total dietary fiber in specific concentrations. Generally the protein can be between 10 and 25 grams per liter of formula, the fat can be of a concentration of between 20 and 45 grams per liter of formula, the carbohydrates (including total dietary fiber) can be of a concentration of between 60 and 110 grams per liter of formula and the dietary fiber as stated above can be of a concentration of between 3.1 and 14.1 grams per liter of formula.

For purposes of this invention, the amount of total dietary fiber was determined using the AOAC method as set forth in Prosky, L, Asp. N-G, Schweizer, TF, DeVries, JH and Furda, I, "Determination of Insoluble, Soluble, and Total Dietary Fiber in Foods and Food Products: Interlaboratory Study", *J. Assoc. Off. Anal. Chem.*, 1988.

It also should be noted that in the following Tables III-V and IX-XVI, "fiber" is included in the listing of "carbohydrate" content. Further, the terms "dietary fiber", "fiber" and "total dietary fiber" for purposes of this invention should be construed as being synonymous unless otherwise defined. Total dietary fiber includes fibers which are both soluble and insoluble, generally including but not limited to lignin, cellulose, pectin, gums, mucilages, algal polysaccharides, and hemicelluloses.

One particular formulation which has been shown to be effective in alleviating the symptoms of infantile colic includes approximately 19.6 grams of protein per liter of formula with the protein source being soy protein isolate, approximately 37.4 grams of fat per liter of formula with the fat source being a blend of soy and coconut oils, and approximately 75.9 grams of carbohydrates (including total dietary fiber) per liter of formula with the carbohydrate source other than that from dietary fiber being sucrose or corn syrup or a blend thereof. In this preferred formula the fat provides 50% of the calories and the carbohydrates (minus that from total dietary fiber) provide 40% of the calories.

Typical fat concentrations of infant formulas have been shown to delay gastric emptying in infants and result in increased incidents of gastroesophageal reflux. Therefore, an alternative embodiment of the formula according to this invention includes approximately 20.3 grams of protein per liter of formula with the protein source being a blend of sodium and calcium caseinates and soy protein isolate, approximately 24.7 grams of fat per liter of formula with the fat source being corn oil, and approximately 106.6 grams of carbohydrates per liter of formula with the carbohydrate source, other than that from dietary fiber, being a blend of sucrose and glucose polymers. In this particular formula the fat provides only 32% of the calories while the carbohydrates (minus that from total dietary fiber) provide 57% of the calories.

Possible sources for the fat in the formula include soy, coconut or corn oil, or another vegetable oil, or a blend thereof while possible sources for the carbohydrates other than that from dietary fiber include sucrose, corn syrup, glucose polymers, or other carbohydrates or a blend thereof.

BEST MODE FOR CARRYING OUT THE INVENTION

In actual use, the formula of this invention is consumed by a colicky infant. The amount consumed does not appreciably differ from that associated with the normal consumption of infant formula.

A representative formula for the infant formula of the invention is set forth in Table III below:

TABLE III

Formula According to the Invention

| Nutrient | Concentration per liter of formula |
|---|---|
| Protein | 13.0–20.3 g |
| Fat | 24.0–38.2 g |
| Carbohydrate | 70.0–110 g |
| Calcium | 510–910 mg |
| Phosphorus | 390–600 mg |
| Magnesium | 50–100 mg |
| Sodium | 190–360 mg |
| Potassium | 730–1100 mg |
| Chloride | 420–575 mg |
| Iron | 8–16 mg |
| Zinc | 5–8 mg |
| Copper | 500–1000 mcg |
| Iodine | 100–510 mcg |
| Manganese | 34–500 mcg |
| Vitamin A | 2000–3800 IU |
| Vitamin D | 400–500 IU |
| Vitamin E | 20–26 IU |
| Vitamin K | 55–200 mcg |
| Vitamin C | 60–200 mg |
| Thiamin | 405–4100 mcg |
| Riboflavin | 610–2000 mcg |
| Pyridoxine | 400–800 mcg |
| Vitamin B-12 | 1.7–6 mcg |
| Niacin | 7–15 mg |
| Folic Acid | 100–275 mcg |
| Pantothenic Acid | 3–7.5 mg |
| Biotin | 30–150 mcg |
| Taurine | 45–70 mg |
| Carnitine | 35–60 mg |
| Choline | 50–202 mg |
| Inositol | 30–100 mg |
| Total Dietary Fiber | 3.1–14.1 g |

The pediatric nutritional formula of this invention is preferably prepared using the following method. An appropriate quantity of protein is dispersed in sufficient water to solubilize it, thereby forming a protein solution. Typically this protein source would be soy protein isolate. A carbohydrate source such as one or more of corn syrup solids, maltodextrins and sucrose is dissolved in water, thereby forming a carbohydrate solution. Appropriate minerals are dissolved in water, so as to form a mineral solution. Also a purified fiber is dispersed in a sufficient quantity of water to form a low viscosity solution.

Once formed, the four solutions (protein, carbohydrate, mineral and fiber) are combined in appropriate quantities with vegetable oils and oil soluble vitamins. This resulting solution is then heat processed and homogenized. Following processing, water soluble vitamins are added. The solution is then diluted with water to the appropriate caloric density, approximately 670–725 kcal per liter of formula. The formula is then dispensed into containers and retorted to obtain commercial sterility. As prepared, the formula contains appropriate nutrients in compliance with the Infant Formula Act as of the date of this application. It should also be recognized that the unique formula of this invention could be prepared for use in powdered form or as a concentrated liquid.

The invention will be better understood in view of the following examples, which are illustrative only and should not be construed as limiting the invention.

EXPERIMENTAL

Determination of Formula Composition

Example 1-Control

The control formula was a commercially available soy-based formula having the following composition.

TABLE IV

| Control Formula | |
|---|---|
| Nutrient | Concentration per liter of formula |
| Protein | 18.6 g |
| Fat | 36.5 g |
| Carbohydrate | 62.3 g |
| Calcium | 817 mg |
| Phosphorus | 527 mg |
| Magnesium | 56 mg |
| Sodium | 314 mg |
| Potassium | 943 mg |
| Chloride | 560 mg |
| Iron | 14 mg |
| Zinc | 6.9 mg |
| Copper | 1.1+ mg |
| Iodine | 0.2+ mg |
| Manganese | 0.3+ mg |
| Vitamin A | 2680 IU |
| Vitamin D | 408+ IU |
| Vitamin E | 22+ IU |
| Vitamin K | 178+ mcg |
| Vitamin C | 126 mg |
| Thiamin | 0.8+ mg |
| Riboflavin | 0.93+ mg |
| Pyridoxine | 0.57 mg |
| Vitamin B-12 | 4.2+ mcg |
| Niacin | 13+ mg |
| Folic Acid | 196+ mcg |
| Pantothenic Acid | 7.2+ mg |
| Biotin | 68+ mcg |
| Taurine | 52+ mg |
| Carnitine | 14+ mg |
| Choline | 118+ mg |
| Inositol | 100+ mg |
| Total Dietary Fiber | 3.1 g |

+Mean batch values, clinical product not analyzed.

EXAMPLE 2 - Invention

The effects of the formula of Example 1 were compared with those of a fiber supplemented product in accordance with this invention. As can be seen by a comparison with the control formula, the compositions were similar except for the addition of fiber and the constituents added to the control formula by the fiber.

TABLE V

| Formula According to the Invention | |
|---|---|
| Nutrient | Concentration per liter of formula |
| Protein | 19.5 g |
| Fat | 38.2 g |
| Carbohydrate | 81.0 g |
| Calcium | 899 mg |
| Phosphorus | 572 mg |
| Magnesium | 76 mg |
| Sodium | 333 mg |
| Potassium | 1078 mg |
| Chloride | 456 mg |
| Iron | 14 mg |
| Zinc | 7.2 mg |
| Copper | 1.2 mg |
| Iodine | 0.2+ mg |
| Manganese | 0.3+ mg |
| Vitamin A | 2750 IU |
| Vitamin D | 408+ IU |
| Vitamin E | 22 IU |
| Vitamin K | 178+ mcg |
| Vitamin C | 86 mg |
| Thiamin | 1.42 mg |
| Riboflavin | 0.86 mg |
| Pyridoxine | 0.56 mg |
| Vitamin B-12 | 4.9 mcg |
| Niacin | 12 mg |
| Folic Acid | 196+ mcg |
| Pantothenic Acid | 7.2+ mg |
| Biotin | 68+ mcg |
| Taurine | 52+ mg |
| Carnitine | 14+ mg |
| Choline | 122+ mg |
| Inositol | 100+ mg |
| Total Dietary Fiber | 14.1 g |

+Mean batch values, clinical product not analyzed.

In this formula, according to the invention, approximately 11 to 12 grams of total dietary fiber per liter of formula is provided by soy polysaccharide. Analysis of several batches of control formula showed that approximately 2.1–3.1 g total dietary fiber is present as an inherent ingredient. Further, the protein source for this formulation is soy protein isolate, the fat source is a blend of soy and coconut oils, and the carbohydrate source, other than that from total dietary fiber, is sucrose, corn syrup or a blend thereof. In comparing nutrient levels with the control formula, additional nutrients are provided by the soy polysaccharide.

EXAMPLE 3

Testing of Soy-based versus Soy-based with Fiber Formulas

The following Study 1 was designed to determine the efficacy of fiber in infant formula in the management of colic.

Infants enrolled in Study 1 had symptoms of colic documented as existing on a soy-based formula. All infants were placed on a commercial soy-based formula (Example 1) for a 6 day baseline period (unblinded). Predominant infant behaviors (crying, fussing, eating, sleeping, awake but content) were recorded by the parents for each 15 minute interval over six successive days. Fussing was defined as "an agitated behavior consisting of considerable motor activity and little vocalization; any vocalization occurring also not awake and content either." Crying was defined as "the highest level of agitation the baby exhibits; the infant gives the impression of extreme distress."

Infants were considered colicky if they cried and/or fussed for more than 3 hours for at least 3 of the 6 days. All infants were at least 2 weeks of age, but not older than B weeks of age prior to initiation of the study. This criterion was used since most colic has been observed to resolve without treatment by 3 to 4 months of age. Also, colicky symptoms which first manifest themselves when infants are older than 8 weeks of age are not likely to be symptoms of true colic, but rather due to other causes.

Study formulas were labeled and boxed so that neither the investigator, parents, nor the study monitor knew the identity of the infant's study formula. Cans were identified only by the study number on the label and one of three blinded codes for each product (total of 6 codes) embossed on the can top. Cases were labeled for each subject for each period. The formulas used were those set forth in Tables IV and V.

Infants returned to the office 7 days following the initial visit. Infants with documented crying and/or fussing for more than 3 hours per day for at least 3 of the 6 days were enrolled in the study. At this second office visit, the parent(s) were given sufficient formula to last until the next scheduled evaluation, 11 days later. The parents were also given a folder containing records to be filled out for the 10 days prior to the next evaluation.

At the end of the first 10-day period, the infant was seen in the home by a member of the research team. Forms were assessed for completeness and the parents were given the second formula and the set of forms to be used during the second 10 days of the study. The infant was seen by the investigator at the end of the second 10-day period for a final evaluation. After the final evaluation, the parent(s) received five cases of the formula that in their judgment better alleviated their infant's symptoms. Infants were seen by the investigator 4 to 5 weeks later.

A total of 27 children were enrolled in and completed Study 1. Of the 27 subjects, 13 were males and 14 were females. Twenty-three of the subjects were Caucasian, one was Black, and three Hispanic. The median age at the first day of the baseline period was 35 days (range 10 to 54 days). The median age colic first appeared was 1.6 weeks (range 0 to 4 weeks). Three subjects were enrolled in the study and were considered protocol failures due to unrelated illnesses occurring during the study period. Data from these three subjects were excluded from the analyses. Of the 27 subjects, 15 were randomized into the sequence of soy-based with fiber followed by soy-based formula, while the other 12 subjects were randomized into the sequence of soy-based followed by soy-based with fiber formula. Infants were studied on soy-based formula for a median of 9 days (range 7 to 10), and for a median of 9 days (range to 10) on soy-based formula with fiber.

Results

Based on the differences in behavior between periods, the results of this study evidence that the soy-based formula with fiber decreases colicky symptoms in a large subgroup of infants. Parents of 18 of the 27 infants (67%) selected the soy-based formula with fiber feeding period as the period when the infant's behavior most improved. The parents of the remaining subjects selected the soy-based formula. Data of the infants whose parents selected the soy-based formula with fiber as the better formula were analyzed to examine the effectiveness of the addition of fiber to infant formula in alleviating colic.

According to the parents who selected the soy-based formula with fiber as the better, the infants were found to fuss, cry, and cry and fuss significantly more while on the soy-based formula than while on the soy-based formula with fiber, with these results being set forth below in Tables VI, VII and VIII, respectively. These same infants slept longer while on the soy-based formula with fiber than while on the soy-based formula, with these results being set forth in Table IX.

TABLE VI

AVERAGE MINUTES FUSSING PER DAY

|  | Baseline | Soy-Based | Soy-Based W/Fiber |
|---|---|---|---|
| Mean | 174 | 163 | 133 |
| Median | 167 | 137 | 114 |
| Minimum | 18 | 62 | 13 |
| Maximum | 330 | 446 | 285 |

TABLE VII

AVERAGE MINUTES CRYING PER DAY

|  | Baseline | Soy-Based | Soy-Based W/Fiber |
|---|---|---|---|
| Mean | 156 | 133 | 91 |
| Median | 151 | 127 | 83 |
| Minimum | 23 | 39 | 0 |
| Maximum | 278 | 324 | 272 |

TABLE VIII

AVERAGE MINUTES CRYING AND FUSSING PER DAY

|  | Baseline | Soy-Based | Soy-Based W/Fiber |
|---|---|---|---|
| Mean | 330 | 297 | 224 |
| Median | 300 | 262 | 182 |
| Minimum | 165 | 146 | 90 |
| Maximum | 548 | 613 | 557 |

TABLE IX

AVERAGE MINUTES SLEEPING PER DAY

|  | Baseline | Soy-Based | Soy-Based W/Fiber |
|---|---|---|---|
| Mean | 802 | 804 | 850 |
| Median | 786 | 822 | 855 |
| Minimum | 634 | 604 | 648 |
| Maximum | 915 | 947 | 1076 |

The percent improvement from baseline for all behaviors was significantly greater while infants consumed the soy-based formula with fiber compared to the soy-based formula as shown below in Tables X, XI, XII and XIII.

TABLE X

DIFFERENT (%) FROM BASELINE FUSSING

|  | Soy-Based | Soy-Based W/Fiber |
|---|---|---|
| Mean | 27 | −14 |
| Median | −7 | −22 |
| Minimum | −67 | −65 |
| Maximum | 529 | 118 |

TABLE XI

| DIFFERENT (%) FROM BASELINE CRYING | | |
|---|---|---|
| | Soy-Based | Soy-Based W/Fiber |
| Mean | 57 | −19 |
| Median | −25 | −49 |
| Minimum | −61 | −100 |
| Maximum | 1338 | 1107 |

TABLE XII

| DIFFERENT (%) FROM BASELINE CRYING AND FUSSING | | |
|---|---|---|
| | Soy-Based | Soy-Based W/Fiber |
| Mean | −7 | −30 |
| Median | −16 | −35 |
| Minimum | −51 | −67 |
| Maximum | 74 | 58 |

TABLE XIII

| DIFFERENT (%) FROM BASELINE SLEEP | | |
|---|---|---|
| | Soy-Based | Soy-Based W/Fiber |
| Mean | 1 | 6 |
| Median | 3 | 10 |
| Minimum | −23 | −17 |
| Maximum | 14 | 21 |

For the fiber preferrers, as can be seen, median minutes of crying, fussing, sleeping, and crying and fussing behaviors were statistically different between the two products. Statistically significant differences in behaviors attributable to formula were not observed for those infants whose parents selected the soy-based formula as the better formula.

The results from this Study 1, from the point of view of stool characteristics, suggested that the soy polysaccharide dose was higher than desirable and/or the degree of colonic fermentation of the fiber in the stool of these infants adversely affected the stool consistency. Generally stools from individuals on high fiber diets are described as bulky, soft, formed, and gassy. The stools of infants while on the soy-based formula with fiber were predominantly more formed to hard than stools passed when they received the soy-based formula.

Concentrations of 14.1 grams or more of total dietary fiber per liter of formula will result in the occurrence of dry, pellet-like, formed/hard stools in a substantial number of infants. Thus, while fiber addition to infant formula appeared to be efficacious in the treatment of colic for a maJority of infants, Study 1 concluded that due to undesirable stool characteristics, total dietary fiber at levels of greater than 14.1 grams per liter of formula would be suboptimal in the treatment of colic.

EXAMPLE 4

Testing of Various Levels of Added Fiber

Based on the conclusion of Study 1 that fiber addition to infant formula appears to be efficacious in the treatment of colic for a majority of infants, a second study sought to ascertain a more optimal treatment level and whether a lower limit existed, taking into account the level ascertained in Study 1 which appears to be a reasonable upper limit.

While this study is presently ongoing, data from 8 completed subjects are available. The criteria for enrollment in this study were the same as those for Study 1. It should be noted that in this study, infants were documented as colicky during a baseline period of 6 days during which they received their habitual formula. There was no attempt to standardize baseline formula, as was done in Study 1. If the infant qualified for the study he/she was enrolled into a controlled, randomized, double-blind, 6-day, triple crossover feeding trial.

It is notable that of the 8 completers, 3 of the infants qualified for the study while receiving a casein hydrolysate formula currently promoted to alleviate colic. Two additional infants who participated in the study had received this same casein hydrolysate formula prior to the baseline without alleviation of symptoms of colic.

The composition of the formulas used in this study, identified for purposes of the study as Formula A, B, and C respectively, are set forth below in Tables XIV, XV, and XVI.

TABLE XIV

| Formula A | |
|---|---|
| Nutrient | Concentration per liter of formula |
| Protein | 18.9 g |
| Fat | 38.0 g |
| Carbohydrate | 68.9 g |
| Calcium | 830 mg |
| Phosphorus | 544 mg |
| Magnesium | 54.6 mg |
| Sodium | 324 mg |
| Potassium | 944 mg |
| Chloride | 463 mg |
| Iron | 13.6 mg |
| Zinc | 6 mg |
| Copper | 0.7 mg |
| Iodine | 0.3 mg |
| Manganese | 0.3 mg |
| Vitamin A | 2848 IU |
| Vitamin D | 430 IU |
| Vitamin E | 22.5 IU |
| Vitamin K | 175 mg |
| Vitamin C | 177 mg |
| Thiamin | 1.41 mg |
| Riboflavin | 0.8 mg |
| Pyridoxine | 0.62 mg |
| Vitamin B-12 | 4.5 mcg |
| Niacin | 11 mg |
| Folic Acid | 190 mcg |
| Pantothenic Acid | 6 mg |
| Biotin | 53 mcg |
| Taurine | 50 mg |
| Carnitine | 13 mg |
| Choline | 130 mg |
| Inositol | 50 mg |
| Total Dietary Fiber | 3.1+ g |

+A negligible quantity of soy polysaccharide was added in addition to inherent content.

TABLE XV

| Formula B | |
|---|---|
| Nutrient | Concentration per liter of formula |
| Protein | 19.6 g |
| Fat | 37.4 g |
| Carbohydrate | 75.9 g |
| Calcium | 884 mg |
| Phosphorus | 573 mg |
| Magnesium | 71.5 mg |
| Sodium | 337 mg |
| Potassium | 1043 mg |
| Chloride | 461 mg |
| Iron | 14.3 mg |
| Zinc | 6 mg |

TABLE XV-continued

Formula B

| Nutrient | Concentration per liter of formula |
|---|---|
| Copper | 0.7 mg |
| Iodine | 0.3 mg |
| Manganese | 0.3 mg |
| Vitamin A | 2822 IU |
| Vitamin D | 430 IU |
| Vitamin E | 22.2 IU |
| Vitamin K | 175 mg |
| Vitamin C | 175 mg |
| Thiamin | 1.48 mg |
| Riboflavin | 0.8 mg |
| Pyridoxine | 0.6 mg |
| Vitamin B-12 | 4.5 mcg |
| Niacin | 11 mg |
| Folic Acid | 190 mcg |
| Pantothenic Acid | 6 mg |
| Biotin | 53 mcg |
| Taurine | 50 mg |
| Carnitine | 13 mg |
| Choline | 130 mg |
| Inositol | 50 mg |
| Total Dietary Fiber | 7.4 g |

TABLE XVI

Formula C

| Nutrient | Concentration per liter of formula |
|---|---|
| Protein | 20.3 g |
| Fat | 24.7 g |
| Carbohydrate | 106.6 g |
| Calcium | 993 mg |
| Phosphorus | 601 mg |
| Magnesium | 93 mg |
| Sodium | 342 mg |
| Potassium | 952 mg |
| Chloride | 489 mg |
| Iron | 15.3 mg |
| Zinc | 6 mg |
| Copper | 0.7 mg |
| Iodine | 0.3 mg |
| Manganese | 0.3 mg |
| Vitamin A | 2944 IU |
| Vitamin D | 430 IU |
| Vitamin E | 21.7 IU |
| Vitamin K | 175 mg |
| Vitamin C | 154 mg |
| Thiamin | 1.45 mg |
| Riboflavin | 0.8 mg |
| Pyridoxine | 0.59 mg |
| Vitamin B-12 | 4.5 mcg |
| Niacin | 11 mg |
| Folic Acid | 190 mcg |
| Pantothenic Acid | 6 mg |
| Biotin | 53 mcg |
| Taurine | 50 mg |
| Carnitine | 13 mg |
| Choline | 130 mg |
| Inositol | 50 mg |
| Total Dietary Fiber | 10.5 g |

As can be seen, the total dietary fiber concentrations of the formulas ranged from 3.1 grams of total dietary fiber per liter of formula for the control product (Formula A) to 7.4 grams and 10.5 grams of total dietary fiber per liter of formula for the two experimental products. The most striking difference between Formulas B and C is in their protein sources and the percentage of total calories from fat and carbohydrate. Formula B is a soy-based formula, identical in most respects to the fiber-containing formula in Study 1, however, Formula B has a lower fiber content. The protein source of Formula C is from caseinates (85%) as well as soy protein (15%). Carbohydrate minus those from dietary fiber provided 57% of the calories and fat 32% of the calories in Formula C, compared to carbohydrate (minus those from dietary fiber) providing 40% of the calories and fat providing 50% of the calories in Formulas A and B.

A total of 8 children were enrolled in and completed the study over a recent six month period. One additional subject was enrolled in the study and was considered a protocol failure due to parental removal. The study was conducted in the same general manner as Study 1. Of the 8 subjects who completed this study, 3 were males and 5 were females. Seven of the subjects were Caucasian and 1 was Black. The median age at the first day of the baseline period was 43 days (range 34 to 49 days). The median age at which colic first appeared was 2.0 weeks (range 1.0 to 2.5 weeks). Since the symptoms of infantile colic often disappear when the infant reaches three to four months of age, the infants chosen for the studies ranged from 2 weeks to 2 months of age, such that even though the study would last one month, they still would not be old enough such that the symptoms could disappear due to the effect of age as opposed to being attributable to the infant formula of this invention.

Results

Parents of four of the infants selected Formula B, while the parents of the other four infants selected Formula C as the formula used when the infant's behavior most improved. No parents selected Formula A. Statistically, selection of a fiber-containing product by all parents is unlikely to have occurred by chance.

The results of the study thus far disclose no observable differences in fussing behavior, with these results being set forth below in Table XVII.

TABLE XVII

AVERAGE TOTAL HOURS FUSSING PER DAY

| | Baseline | Formula A | Formula B | Formula C |
|---|---|---|---|---|
| Mean | 3.9 | 3.1 | 2.7 | 3.1 |
| Median | 3.8 | 3.2 | 3.3 | 3.8 |
| Minimum | 2.5 | 1.3 | 0.5 | 0.2 |
| Maximum | 5.3 | 4.8 | 4.8 | 4.5 |

However, infants appeared to cry less on Formulas B and C, the two high-fiber formulas, compared to the baseline period or while on Formula A as can be seen by Table XVIII set forth below.

TABLE XVIII

AVERAGE TOTAL HOURS CRYING PER DAY

| | Baseline | Formula A | Formula B | Formula C |
|---|---|---|---|---|
| Mean | 2.8 | 2.2 | 1.9 | 0.9 |
| Median | 2.2 | 2.1 | 0.9 | 0.6 |
| Minimum | 0.5 | 0.1 | 0.3 | 0.0 |
| Maximum | 6.0 | 7.5 | 4.8 | 2.2 |

It also appears that infants cry and fuss less, and sleep longer while on Formula C than while on the other formulas, with these data set forth below in Tables XIX and XX respectively.

TABLE XIX

AVERAGE TOTAL HOURS CRYING AND FUSSING PER DAY

| | Baseline | Formula A | Formula B | Formula C |
|---|---|---|---|---|
| Mean | 6.7 | 5.3 | 4.6 | 4.1 |
| Median | 6.6 | 5.6 | 5.2 | 4.0 |

TABLE XIX-continued

| AVERAGE TOTAL HOURS CRYING AND FUSSING PER DAY | | | | |
|---|---|---|---|---|
| | Baseline | Formula A | Formula B | Formula C |
| Minimum | 3.0 | 1.6 | 1.2 | 0.4 |
| Maximum | 10.6 | 9.6 | 8.0 | 6.7 |

TABLE XX

| AVERAGE TOTAL HOURS SLEEP PER DAY | | | | |
|---|---|---|---|---|
| | Baseline | Formula A | Formula B | Formula C |
| Mean | 12.4 | 13.4 | 13.7 | 14.4 |
| Median | 12.9 | 13.8 | 13.1 | 14.4 |
| Minimum | 7.3 | 9.6 | 12.0 | 12.1 |
| Maximum | 15.0 | 16.5 | 16.5 | 17.8 |

Stool characteristics were compared in view of the findings in Study 1. Predominant stool consistencies are shown in Table XXI which is set forth below.

TABLE XXI

| AVERAGE DAILY RANKED STOOL CONSISTENCY | | | | |
|---|---|---|---|---|
| | Baseline | Formula A | Formula B | Formula C |
| Mean | 1.9 | 2.3 | 2.9 | 3.1 |
| Median | 1.9 | 2.3 | 2.9 | 3.1 |
| Minimum | 1.0 | 1.0 | 2.0 | 2.1 |
| Maximum | 2.7 | 3.6 | 4.0 | 3.8 |

1 = Watery
2 = Soft
3 = Formed
4 = Hard

Watery and soft stools comprised the majority of stools during the baseline period. The predominant stool consistency was soft for infants when they were on Formula A, whereas it was formed for infants when they were on Formulas B and C. One infant had hard stools while on all three study formulas. Additionally one other infant had hard stools while on Formula C. Thus, the percentage of hard stools while on the high-fiber containing formulas in this study was lower than that observed with the higher fiber containing formula in Study 1.

The results from these experiments demonstrate that the infant formula of this invention is effective in treating colicky infants. The fiber level of the formulas in the second study, 7.4–10.5 g/L, are more optimal from the point of view of stool characteristics. Additionally, the formula is nutritionally complete as an infant formula. The manufacture of the formula utilizes conventional equipment and may be readily accomplished.

While the infant formula and method of making said formula herein described constitute a preferred embodiment of this invention, it is to be understood that the invention is not limited to this precise form of apparatus or method and that changes may be made therein without departing from the scope of the invention which is defined in the appended claims.

What is claimed is:

1. An infant formula, said formula comprising:
   1) protein, said protein being of a concentration of between 10 and 25 grams per liter of formula;
   2) fat, said fat being of a concentration of between 20 and 45 grams per liter of formula;
   3) carbohydrates, said carbohydrates including those from total dietary fiber being of a concentration of between 60 and 110 grams per liter of formula; and
   4) total dietary fiber, said fiber being of a concentration of above 3.1 and below 14.1 grams per liter of formula and wherein the source of said fiber is soy polysaccharide derived from soy beans.

2. The formula as claimed in claim 1 wherein said protein is of a concentration of between 15 and 21 grams per liter of formula, said fat is of a concentration of between 23 and 40 grams per liter of formula, and said carbohydrates including total dietary fiber are of a concentration of between 70 and 110 grams per liter of formula.

3. The formula as claimed in claim 2 wherein said protein has as its source soy protein isolate, or sodium and calcium caseinates or a blend thereof, said fat has as its source soy, coconut or corn oil or another vegetable oil or a blend thereof, and said carbohydrates other than total dietary fiber have as their source sucrose, corn syrup, glucose polymers, other carbohydrates or a blend thereof.

4. The formula as claimed in claim 1 wherein said protein is of a concentration of between 15 and 20 grams per liter of formula, said fat is of a concentration of between 24 and 38 grams per liter of formula, said carbohydrates including total dietary fiber are of a concentration of between 75 and 110 grams per liter of formula, and said total dietary fiber is of a concentration of between 3.5 and 14.0 grams per liter of formula.

5. The formula as claimed in claim 1 wherein said protein is of a concentration of approximately 19.6 grams per liter of formula and has as its source soy protein isolate, said fat is of a concentration of approximately 37.4 grams per liter of formula and has as its source a blend of soy and coconut oils, and said carbohydrates including total dietary fiber are of a concentration of approximately 75.9 grams per liter of formula and except for those from dietary fiber have as their source sucrose or corn syrup or a blend thereof.

6. The formula as claimed in claim 1 wherein said protein is of a concentration of approximately 20.3 grams per liter of formula and has as its source a blend of sodium and calcium caseinates and soy protein isolate, said fat is of a concentration of approximately 24.7 grams per liter of formula and has as its source corn oil, and said carbohydrates including total dietary fiber are of a concentration of approximately 106.6 grams per liter of formula and with the exception of those from the fiber have as their source a blend of sucrose and glucose polymers.

7. The formula as claimed in claim 1 wherein said fat provides 50% of the calories and said carbohydrates minus those from total dietary fiber provide 40% of the calories in said formula.

8. The formula as claimed in claim 1 wherein said fat provides 32% of the calories and said carbohydrates minus those from total dietary fiber provide 57% of the calories in said formula.

9. A method of treating infants with colic, said method consists of feeding an infant in need of treatment a formula, the improvement comprising a formula consisting essentially of:
   1) protein, said protein being of a concentrating of between 10 and grams per liter of formula;
   2) fat, said fat being of a concentration of between 20 and 45 grams per liter of formula;
   3) carbohydrates, said carbohydrates including total dietary fiber being of a concentration of between 60 and 110 grams per liter of formula; and
   4) total dietary fiber, said fiber being of a concentration of above 3.1 and below 14.1 grams per liter of formula and wherein said fiber is soy polysaccharide derived from soy beans.

10. The formula as claimed in claim 9 wherein said protein is of a concentration of between 15 and 21 grams per liter of formula, said fat is of a concentration of between 23 and 40 grams per liter of formula, and said carbohydrates including total dietary fiber are of a concentration of between 70 and 110 grams per liter of formula.

11. The formula as claimed in claim 10 wherein said protein has as its source soy protein isolate, or sodium and calcium caseinates or a blend thereof, said fat has as its source soy, coconut or corn oil or another vegetable oil or a blend thereof, and said carbohydrates other than those from dietary fiber have as their source sucrose, corn syrup, glucose polymers, other carbohydrates or a blend thereof.

12. The formula as claimed in claim 9 wherein said protein is of a concentration of between 15 and 20 grams per liter of formula, said fat is of a concentration of between 24 and 38 grams per liter of formula, said carbohydrates including total dietary fiber are of a concentration of between 75 and 110 grams per liter of formula, and said total dietary fiber is of a concentration of between 3.5 and 14.0 grams per liter of formula.

13. The formula as claimed in claim 9 wherein said protein is of a concentration of approximately 19.6 grams per liter of formula and has as its source soy protein isolate, said fat is of a concentration of approximately 37.4 grams per liter of formula and has as its source a blend of soy and coconut oils, and said carbohydrates including total dietary fiber are of a concentration of approximately 75.9 grams per liter of formula and with the exception of those from the fiber have as their source sucrose or corn syrup or a blend thereof.

14. The formula as claimed in claim 9 wherein said protein is of a concentration of approximately 20.3 grams per liter of formula and has as its source a blend of sodium and/or calcium caseinates and soy protein isolate, said fat is of a concentration of approximately 24.7 grams per liter of formula and has as its source corn oil, and said carbohydrates including total dietary fiber are of a concentration of approximately 106.6 grams per liter of formula and with the exception of those from the fiber have as their source a blend of sucrose and glucose polymers.

15. The formula as claimed in claim 9 wherein said fat provides 50% of the calories and said carbohydrates minus that from dietary fiber provide 40% of the calories in said formula.

16. The formula as claimed in claim 9 wherein said fat provides 32% of the calories and said carbohydrates minus that from dietary fiber provide 57% of the calories in said formula.

17. A method for manufacturing infant formula, said method comprising the steps of:
1) dispersing an appropriate quantity of a protein source in water sufficient to solubilize the protein, thereby forming a protein solution;
2) dissolving carbohydrates in water, thereby forming a carbohydrate solution;
3) mixing minerals in water, thereby forming a mineral solution;
4) dispersing soy polysaccharide fiber in a sufficient quantity of water to form a low viscosity solution, thereby forming a fiber solution;
5) combining appropriate quantities of said protein solution, said carbohydrate solution, said mineral solution, said fiber solution, and a solution of vegetable oil containing oil soluble vitamins;
6) heat processing and homogenizing the combined solution;
7) adding water soluble vitamins to the combined solution; and
8) adding water to dilute the combined solution to the desired caloric density, such that the total dietary fiber content of said formula is above 3.1 and below 14.1 grams per liter of formula.

* * * * *

UNITED STATES PATENT AND TRADEMARK OFFICE
CERTIFICATE OF CORRECTION

PATENT NO. : 5,021,245

DATED : June 4, 1991

INVENTOR(S) : Marlene W. Borschel, John D. Benson, Merle D. Breen, William C. MacLean, Jr., Debra L. Ponder, Alan D. Strickland, William A. Treem It is certified that error appears in the above-identified patent and that said Letters Patent is hereby corrected as shown below:

Column 2 Line 27 "1]" to --1)--
Column 3 Line 32 "4]" to --4)--
Column 5 Line 21 "wi&h" to --with--
Column 6 Line 39 "Apparatus," to --(Apparatus,--
Column 6 Line 61 "Taper," to --Taper, LJ,--
Column 7 Line 56 "fiber]" to --fiber)--
Column 10 Line 59 "(unblinded]." to --(unblinded)--
Column 11 Line 4 "B" to --8--
Column 11 Line 44 "days] to --days)--
Column 11 Line 45 "weeks]" to --weeks)--
Column 11 Line 55 "10]" to --10)--
Column 11 Line 55 "(range to 10)" to --(range 7 to 10)--
Column 13 Line 51 "maJority" to --majority--
Column 16 Line 3 "(15%]" to --(15%)--
Column 16 Line 16 "(range 34 to 49 days]." to --(range 34 to 49 days).--
Column 16 Line 18 "(range 1.0 to 2.5 weeks]." to --(range 1.0 to 2.5 weeks).--
Column 18 Line 61 "between 10 and grams" to --between 10 and 25 grams--

Signed and Sealed this

Twenty-fourth Day of November, 1992

Attest:

DOUGLAS B. COMER

*Attesting Officer*   *Acting Commissioner of Patents and Trademarks*